(12) United States Patent
Bischoff et al.

(10) Patent No.: US 11,033,980 B2
(45) Date of Patent: *Jun. 15, 2021

(54) DEVICE AND METHOD FOR MATERIAL PROCESSING BY MEANS OF LASER RADIATION

(71) Applicant: Carl Zeiss Meditec AG, Jena (DE)

(72) Inventors: Mark Bischoff, Jena (DE); Dirk Muehlhoff, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 2540 days.

This patent is subject to a terminal disclaimer.

(21) Appl. No.: 13/715,670

(22) Filed: Dec. 14, 2012

(65) Prior Publication Data
US 2013/0119029 A1    May 16, 2013

Related U.S. Application Data

(62) Division of application No. 11/549,478, filed on Oct. 13, 2006, now abandoned.
(Continued)

(51) Int. Cl.
*B23K 26/02* (2014.01)
*B23K 26/08* (2014.01)
(Continued)

(52) U.S. Cl.
CPC .......... *B23K 26/02* (2013.01); *A61F 9/00827* (2013.01); *B23K 26/035* (2015.10);
(Continued)

(58) Field of Classification Search
CPC ............. A61F 9/00827; A61F 9/00836; B23K 26/0635; B23K 26/0876
(Continued)

(56) References Cited

U.S. PATENT DOCUMENTS 3,948,248 A * 4/1976 Zuckerman ........ A61B 5/02216
                                                                 600/489
4,988,348 A * 1/1991 Bille ........................ A61F 9/008
                                                                 128/898
(Continued)

FOREIGN PATENT DOCUMENTS

DE    10 2005 049 281 A1    4/2007
EP         1 731 120 A1    12/2006
(Continued)

OTHER PUBLICATIONS

Heisterkamp et al., "Instrastromal refractive surgery with ultrashort laser pulses: in vivo study on the rabbit eye", Graefe's Arch Clin Exp Ophthalmol, 2003, 241:511-517.
(Continued)

*Primary Examiner* — Gary Jackson
*Assistant Examiner* — Anant A Gupta
(74) *Attorney, Agent, or Firm* — Patterson Thuente Pedersen, P.A.

(57) ABSTRACT

A device for material processing by laser radiation, including a source of laser radiation emitting pulsed laser radiation for interaction with the material, optics focusing the pulsed processing laser radiation to a center of interaction in the material, and a scanning unit shifting the positions of the center of interaction within the material. Each processing laser pulse interacting with the material in a zone surrounding the center of interaction assigned to the laser pulse so that material is separated in the zones of interaction. A control unit controls the scanning unit and the source of laser radiation such that a cut surface is produced in the material by sequential arrangement of zones of interaction. The control unit controls the source of laser radiation and the scanning unit such that adjacent centers of interaction are located at a spatial distance a ≤10 μm from each other.

18 Claims, 5 Drawing Sheets

Related U.S. Application Data

(60) Provisional application No. 60/726,887, filed on Oct. 14, 2005.

(51) Int. Cl.
*A61F 9/008* (2006.01)
*B23K 26/0622* (2014.01)
*B23K 26/035* (2014.01)

(52) U.S. Cl.
CPC ...... *B23K 26/0624* (2015.10); *B23K 26/0876* (2013.01); *A61F 2009/00872* (2013.01); *A61F 2009/00897* (2013.01)

(58) Field of Classification Search
USPC .............................. 606/4–6, 10–14
See application file for complete search history.

(56) References Cited

U.S. PATENT DOCUMENTS

| | | | |
|---|---|---|---|
| 5,284,477 A | 2/1994 | Hanna et al. | |
| 5,656,186 A | 8/1997 | Mourou et al. | |
| 5,928,221 A | 7/1999 | Sasnett et al. | |
| 5,984,916 A * | 11/1999 | Lai | B23K 26/0624 606/10 |
| 5,993,438 A | 11/1999 | Juhasz et al. | |
| 6,080,144 A | 6/2000 | O'Donnell, Jr. | |
| 6,090,100 A * | 7/2000 | Hohla | A61F 9/008 606/10 |
| 6,146,375 A | 11/2000 | Juhasz et al. | |
| 6,210,401 B1 | 4/2001 | Lai | |
| 6,585,722 B1 * | 7/2003 | Abe | A61F 9/008 606/10 |
| 6,585,916 B2 | 7/2003 | Sanada et al. | |
| 7,131,968 B2 | 11/2006 | Bendett et al. | |
| 7,351,241 B2 | 4/2008 | Bendett et al. | |
| 2003/0014042 A1 | 1/2003 | Juhasz et al. | |
| 2003/0212387 A1 | 11/2003 | Kurtz et al. | |
| 2004/0019346 A1 * | 1/2004 | Chernyak | A61F 9/008 606/5 |
| 2004/0102765 A1 | 5/2004 | Koenig | |
| 2005/0107773 A1 | 5/2005 | Bergt et al. | |
| 2005/0165387 A1 | 7/2005 | Lubatschowski et al. | |
| 2007/0010804 A1 | 1/2007 | Rathjen et al. | |
| 2007/0055221 A1 | 3/2007 | Lubatschowski et al. | |
| 2007/0179483 A1 | 8/2007 | Muhlhoff et al. | |
| 2009/0294422 A1 * | 12/2009 | Lubatschowski | B23K 26/0626 219/121.72 |

FOREIGN PATENT DOCUMENTS

| | | |
|---|---|---|
| JP | H 03-7152 A | 1/1991 |
| JP | 2003210514 | 7/2003 |

OTHER PUBLICATIONS

Homolka et al, "Laser shaping of corneal transplants in vitro: area ablation with small overlapping laser spots produced by a pulsed scanning laser beam using an optimizing ablation algorithm", Phys. Med. Biol., 44, 1999, pp. 1169-1180.

Juhasz et al., "Corneal Refractive Surgery with Femtosecond Lasers", IEEE Journal of Selected Topics in Quantum Electronics, vol. 5, No. 4, Jul./Aug. 1999, pp. 902-910.

Ripken et al., "First in-vivo studies of presbyopia treatment with ultrashort laserpulses", Proc. of SPIE, vol. 5142, 2003, pp. 137-145.

European Search Report for European Application No. EP 17 16 6441 dated Aug. 2, 2017, 2 pages.

\* cited by examiner

DEVICE AND METHOD FOR MATERIAL PROCESSING BY MEANS OF LASER RADIATION

RELATED APPLICATIONS

The present application is a Division of U.S. application Ser. No. 11/549,478, filed Oct. 13, 2006 now abandoned, which application claims the benefit of U.S. Provisional Application No. 60/726,887, filed Oct. 14, 2005, which applications are incorporated herein in their entirety by reference.

FIELD OF THE INVENTION

The invention relates to a device for material processing by means of laser radiation, said device comprising a source of laser radiation emitting pulsed laser radiation for interaction with the material; optics focusing the pulsed processing laser radiation to a center of interaction in the material; a scanning unit shifting the positions of the center of interaction within the material, wherein each processing laser pulse interacts with the material in a zone surrounding the center of interaction assigned to said laser pulse so that material is separated in the zones of interaction; and a control unit which controls the scanning unit and the source of laser radiation such that a cut surface is produced in the material by sequential arrangement of zones of interaction.

BACKGROUND OF THE INVENTION

The invention further relates to a method of material processing by means of laser radiation, wherein pulsed processing laser radiation is generated, focused for interaction to centers of interaction in the material, and the positions of the centers of interaction in the material are shifted, wherein each processing laser pulse interacts with the material in a zone surrounding the center of interaction assigned to said laser pulse and material is separated in the zones of interaction and a cut surface is produced in the material by sequential arrangement of zones of interaction.

The invention further relates to a device for material processing by means of laser radiation, said device comprising a source of laser radiation emitting pulsed laser radiation for interaction with the material; optics focusing the pulsed processing laser radiation along an optical axis to a center of interaction in the material; a scanning unit shifting the positions of the center of interaction within the material, wherein each processing laser pulse interacts with the material in a zone surrounding the center of interaction assigned to said laser pulse so that material is separated in the zones of interaction; and a control unit which controls the scanning unit and the source of laser radiation such that a cut surface is produced in the material by sequential arrangement of zones of interaction.

The invention still further relates to a method of material processing by means of laser radiation, wherein pulsed processing laser radiation is generated and focused for interaction to centers of interaction in the material along an optical axis, and the positions of the centers of interaction in the material are shifted, wherein each processing laser pulse interacts with the material in a zone surrounding the center of interaction assigned to said laser pulse, and material is separated in the zones of interaction, and a cut surface is produced in the material by sequential arrangement of zones of interaction.

These devices as well as corresponding methods of material processing are particularly suitable to produce curved cut surfaces within a transparent material. Curved cut surfaces are produced, for example, in laser-surgical methods and, in particular, in ophthalmic operations. In doing so, treatment laser radiation is focused into the tissue, i.e. below the surface of the tissue, to a center of interaction. Material layers in a surrounding zone of interaction are separated thereby. The zone usually corresponds to the focus spot. The laser pulse energy is usually selected such that an optical breakthrough in the tissue forms in the zone of interaction.

In the tissue, a plurality of processes initiated by the laser radiation pulse take place in a time sequence after an optical breakthrough. First, the optical breakthrough generates a plasma bubble in the material. Once such plasma bubble has formed, it grows due to expanding gas. Next, the gas generated in the plasma bubble is absorbed by the surrounding material and the bubble disappears again. However, this process takes very much longer than the forming of the bubble itself. If a plasma is generated at a material interface which may even be located within a material structure, material removal is effected from said interface. This is then referred to as photoablation. In case of a plasma bubble separating previously connected material layers, one usually speaks of photodisruption. For the sake of simplicity, all such processes are summarized here by the term "interaction", i.e. this term includes not only the optical breakthrough, but also any other material-separating effects.

For high precision of a laser-surgical method, it is indispensable to ensure high localization of the effect of laser beams and to avoid, if possible, collateral damage to adjacent tissue. Therefore, it is common in the prior art to apply the laser radiation in pulsed form so that the threshold value for the energy density required to initiate an optical breakthrough is exceeded only in the individual pulses. In this respect, U.S. Pat. No. 5,984,916 clearly shows that the spatial extent of the zone of interaction substantially depends on the pulse duration only as long as a pulse duration of 2 ps is exceeded. For values of few 100 fs, the size of the zone of interaction is almost independent of the pulse duration. Thus, high focusing of the laser beam in combination with very short pulses, i.e. below 1 ps, allows the zone of interaction to be inserted in a material with pinpoint accuracy.

The use of such pulsed laser radiation has recently become established, in particular, for laser-surgical correction of visual deficiencies in ophthalmology. Visual deficiencies of the eye are often due to the fact that the refractive properties of the cornea and of the lens do not cause optimal focusing on the retina. This type of pulsing is also the subject matter of the invention described herein.

The aforementioned U.S. Pat. No. 5,984,916 describes a method of producing a cut surface by suitably generating optical breakthroughs, thereby ultimately exerting a selective influence on the diffractive properties of the cornea. A multiplicity of optical breakthroughs are sequentially arranged such that the cut surface isolates a lens-shaped partial volume within the cornea of the eye. The lens-shaped partial volume separated from the remaining corneal tissue is then removed from the cornea via a laterally opening cut. The shape of the partial volume is selected such that upon removal the shape and, thus, the refractive properties of the cornea are changed so as to cause the desired correction of a visual deficiency. The cut surface required here is curved and circumscribes the partial volume, thus necessitating three-dimensional shifting of the focus. Therefore, two-dimensional deflection of the laser radiation is combined with simultaneous shifting of the focus in a third spatial direction. This is summarized here by the terms "scanning", "shifting" or "deflecting".

When composing the cut surface by sequential arrangement of optical breakthroughs in the material, an optical breakthrough is generated many times faster than the time it takes until a plasma generated thereby is absorbed by the tissue again. It is known from the publication of A. Heisterkamp et al., Der Ophthalmologe, 2001, 98:623-628, that, after an optical breakthrough has been generated, a plasma bubble forms in the eye's cornea at the focal point where the optical breakthrough was generated, which plasma bubble can grow together with adjacent bubbles to form macrobubbles. The publication explains that the joining of still growing plasma bubbles reduces the quality of the cut. Therefore, said publication proposes a method wherein individual plasma bubbles are not generated immediately adjacent to each other. Instead, a gap is left in a spiral-shaped profile between sequentially generated optical breakthroughs, which gap is filled with optical breakthroughs and the resulting plasma bubbles in a second pass through the spiral. This is intended to prevent joining of adjacent plasma bubbles and to improve the quality of the cut.

In order to achieve good quality of the cut, the prior art thus uses defined sequences in which the optical breakthroughs are generated. This is intended to prevent joining of growing plasma bubbles. Since a cut is desired, of course, wherein as few bridges as possible connect the material or the tissue, respectively, the plasma bubbles generated ultimately have to grow together in any case to form a cut surface. Otherwise, the material connections would remain and the cut would be incomplete.

Therefore, it is an object of the invention to generate good-quality cuts in the material without having to observe defined sequences when introducing laser pulses.

According to the invention, this object is achieved in a first variant by a device of the first-mentioned generic type, wherein the control unit controls the source of laser radiation and the scanning unit such that adjacent centers of interaction are located at a spatial distance a $\leq 10$ μm from each other. In the first variant, the object is further achieved by a method of the first-mentioned generic type, wherein adjacent centers of interaction are located at a spatial distance a $\leq 10$ μm.

In a second variant of the invention, the object is achieved by a device of the first-mentioned generic type, wherein the fluence F of the pulses for each center of interaction is respectively below 5 J/cm$^2$. In the second variant, the object is also achieved by a method of the first-mentioned generic type, wherein the zones of interaction are exposed to pulses whose fluence F is respectively below 5 J/cm$^2$.

In a third variant of the invention, the object is achieved by a device of the second-mentioned generic type, wherein the control unit controls the source of laser radiation and the scanning unit such that the cut surface comprises two portions located adjacent to each other along the optical axis, and at least partially illuminates them with laser pulses applied within a time interval t$\leq 5$ s. Also in the third variant the object is achieved by a method of the second-mentioned type, wherein the cut surface comprises two portions located adjacent to each other along the optical axis which are at least partially exposed to laser pulses applied within a time interval t$\leq 5$ s.

The invention is based on the finding that zones of interaction in the material influence each other. Thus, the effect of a laser beam pulse depends on the extent to which previous laser exposures already took place in the vicinity of the center of interaction. From this, the inventors concluded that the pulse energy required to generate an optical breakthrough or to cause material separation depends on the distance from the nearest center of interaction. All of the variants according to the invention take advantage of this finding.

The inventive minimization of the distance between centers of interaction, e.g. of the distance between the focus positions of adjacent optical breakthroughs, according to variant 1 allows the processing pulse energy to be decreased. The parameter describing the pulse energy is the fluence, i. e. the energy per area or the areal density of energy. Thus, the inventive variant 1 with a distance of less than 10 μm addresses an aspect of the finding attributable for the first time to the inventors.

Another aspect is that the fluence of the processing laser pulses is now significantly reduced. Thus, variant 2 relates to the same aspect as variant 1, although it does not prescribe an upper limit for the distance, but for the fluence.

Accordingly, all variants of the invention provide basic conditions for producing a cut by introducing pulsed laser radiation, said basic conditions taking into consideration the effects of the immediately adjacent introduced pulse. Regarding the pulse length, the teaching of U.S. Pat. No. 5,984,916 is applied here, i.e. pulses below 1 ps, preferably few 100 fs, e. g. 300-500 fs, are used. As far as the invention defines an upper limit of the distance, this refers to the distance from the closest center of interaction. Since a cut surface is usually produced by a multiplicity of sequentially arranged centers of interaction, the distance may be understood, for the sake of simplicity, also to be the mean value of the laser focus spacing for the laser pulses in the material. If the grating of centers of interaction which is substantially two-dimensional along a cut surface is not symmetrical, distance can also be the characteristic mean spacing. It is known in the prior art to use a pulsed source of laser radiation and to modify some of the laser pulses emitted by said source such that they do not cause a processing effect in the material. Only some of the laser radiation pulses will then be used for processing. Whenever the present description uses the term "laser radiation pulse", "laser pulse" or "pulse", this always means a processing laser pulse, i.e. a laser radiation pulse provided or formed or suitable for interaction with the material.

The complexity of equipment is reduced by the invention, because the pulse peak performance decreases. Due to the reduced distance of the centers of interaction, the pulse repetition frequency increases if the processing duration is to be kept constant. Further, smaller plasma bubbles are produced in the case of optical breakthroughs, thus making the cut thinner. However, the prior art always worked with comparatively large distances between the centers of interaction and the fluence of the pulses was selected suitably high in order to securely obtain optical breakthroughs and large plasma bubbles suitably adapted to the distances.

At the same time, a lower fluence also reduces personnel hazards during material processing. This is of essential importance in ophthalmic methods. It turns out to be particularly advantageous that it is now possible to work with lasers of hazard class 1M, whereas class 3 was required in the prior art. This class required operating personnel, for example a physician or a nurse, to wear protective goggles, which naturally makes patients feel uneasy. Such protective measures are no longer necessary with the lasers of class 1M that are now possible according to the invention.

Therefore, the invention also provides as a further embodiment, or independently, a device for material processing by means of laser radiation, said device comprising an emitting source of laser radiation which emits pulsed laser radiation for interaction with the material, optics focusing the pulsed laser radiation to a center of interaction in the material, a scanning unit shifting the position of the center of interaction in the material, wherein each processing laser pulse interacts with the material in a zone surrounding the center of interaction assigned to said pulse, so that material is separated in the zones of interaction, and said device further comprising a control unit controlling the scanning unit and the source of laser radiation such that a cut surface is produced in the material by sequential arrangement of zones of interaction, wherein a laser of a hazard class below 3, preferably a laser of hazard class 1M, is employed. The indication of the hazard class relates to International Standard IEC 60825-1 in its version as effective Oct. 13, 2005. Analogously, there is provided (independently or as a further embodiment) a device for material processing by means of laser radiation, said device comprising a source of laser radiation emitting pulsed laser radiation for interaction with the material; optics focusing the pulsed laser radiation to a center of interaction in the material along an optical axis; a scanning unit shifting the position of the center of interaction in the material, each laser pulse interacting with the material in a zone surrounding the centers of interaction assigned to said pulse and material being separated in the zones of interaction, said device further comprising a control unit controlling the scanning unit and the source of laser radiation such that a cut surface is produced in the material by sequential arrangement of zones of interaction, wherein a laser of a hazard class below 3, preferably a laser of hazard class 1M, is used. This is also useful as a further embodiment for each of the aforementioned devices or for each of the aforementioned methods, respectively. Unless explicitly indicated otherwise, this shall apply to each described advantageous design, further embodiment or realization.

Tests carried out by the inventors have shown that an optical breakthrough sets in only above a defined threshold value M which is a function of the distance a of adjacent centers of interaction according to the equation $M = 3.3 \text{ J/cm}^2 - (2.4 \text{ J/cm}^2)/(1+(a/r)^2)$. An optical breakthrough is ensured for each individual laser pulse only at a pulse fluence above the threshold value M. The parameter r appearing in said equation represents an experimentally recognized average range of the influence of adjacent zones of interaction. Depending on the application, there may be fluctuations here, so that a variation of the value between 3 and 10 μm is possible; preferably, $r = 5$ μm.

In a further embodiment of the invention, the upper limit of pulse fluence mentioned for variant 2 of the invention will also be based on the aforementioned dependence of the threshold value on the distance of adjacent centers of interaction. Therefore, a further embodiment is preferred in which fluence exceeds the threshold value M by an excessive energy of no more than 3 J/cm$^2$. The range defined thereby provides a particularly good quality of the cut, while initiation of an optical breakthrough is ensured at the same time. If the excessive energy were further increased, unnecessarily large plasma bubbles would be generated and the quality of the cut would deteriorate.

However, producing a cut now no longer stringently requires working with optical breakthroughs. The inventors have found that, if the zones of interaction overlap, material can be separated and, thus, a cut surface can be formed even at energies of the pulsed laser radiation below a threshold value for initiation of an optical breakthrough. Therefore, a further embodiment is provided wherein the spatial distance a of the centers of interaction of two sequential pulses is smaller than the size of the focus d, so that there is a mutual overlap of volumes of the material that are sequentially irradiated with laser radiation, i.e. zones of interaction. This embodiment results in material separation without formation of plasma bubbles, which leads to a particularly smooth cut.

Advantageously, the fluence of the laser pulse can then also be decreased below the already explained threshold value, because a tissue-separating effect is still achieved due to overlapping of zones of interaction. The individual laser pulse then no longer securely generates an optical breakthrough; the separation of tissue is caused only if the zones of interaction overlap. This allows pulse energies that are orders of magnitude below those of the state of the art; at the same time the quality of the cut is increased again, because zones of interaction, which are generated sequentially in time, overlap. Thus, the distance of the centers of interaction ranges from zero to the diameter of the focus, which is e.g. between 1 and 5 μm considering the $1/e^2$ diameter (e=Euler's constant).

Cutting according to the invention produces a very fine cut because, due to the reduced distance or the reduced pulse energy, respectively, correspondingly small or even no plasma bubbles are worked with or can be worked with. However, a fine cut surface can also be a disadvantage, e.g. if a surgeon wants to optically recognize at least part of the cut surface. This is the case, for example, in laser surgery according to the fs-LASIK method. The partial volume isolated therein by the action of laser radiation, which volume is to be removed from the tissue by a lateral cut, is usually freed first from any residual bridges to the surrounding material by the surgeon using a spatula. For this purpose, the surgeon pushes the spatula into the pocket formed by the laterally opening cut and traces the partial volume with the spatula. In case of a very fine, i.e. smooth cut surface, it may occur that the surgeon can no longer see the profile of the cut surface in the material from outside. Therefore, he will not know where the periphery of the partial volume lies and will not be able to securely guide the spatula. In order to solve these problems, a method of the above-mentioned type is provided wherein the cut surface is divided into at least two partial surfaces, and one partial surface is formed with operating parameters that generate a coarser and, thus, rougher cut surface. In a device of the above-mentioned type, the control unit carries out the corresponding control of the laser source and of the scanning unit. Preferably, said coarser cut surface will be placed on the periphery, which is easily recognizable for the user and is of no importance to the quality of the cut surface, e.g. in ophthalmic surgery. Thus, the two partial surfaces differ from each other with respect to at least one parameter influencing the fineness of the cut surface. For instance, a possible parameter is the fluence of the laser pulses used or the spatial distance between the centers of interaction.

Combining this approach, which may be principally effected in different ways and is not restricted to the invention described herein, with one of the aforementioned variants of the invention, it is convenient for the control unit to control the source of laser radiation and the scanning unit such that the cut surface is composed of at least a first and a second partial cut surface, the first partial cut surface being produced by controlling the source of laser radiation and the scanning unit according to one of the aforementioned inventive concepts, and the second partial cut surface being produced by controlling the source of laser radiation so as to cause a pulse fluence of more than 3 J/cm$^2$, preferably more than 5 J/cm$^2$. Of course, a >10 μm may be set then, because the plasma bubbles will be large. The latter partial surface then automatically has the desired coarser structure and facilitates recognition of the cut surface by the user or surgeon. The analogous method accordingly provides for the second partial cut surface to be produced by a method of the invention at a pulse fluence of more than 3 J/cm$^2$, preferably more than 5 J/cm$^2$.

Conveniently, the coarser partial surface will be selected such that it surrounds the finer partial surface, so that the surgeon can clearly recognize the periphery of the cut surface and optical imaging at the treated eye (in the case of ophthalmic surgery) is not adversely affected.

The finding upon which the invention is based further shows that the threshold value required to securely achieve an optical breakthrough decreases as the distance of the centers of interaction decreases.

The analysis carried out by the inventors further shows that the shape of the plasma bubbles generated, which are formed as a result of the interaction of the laser pulses with the material or the tissue, respectively, can be subject to a temporal change, as also indicated in the publication by Heisterkamp et al. However, whereas this publication focuses on preventing a center of interaction from being located near a just growing plasma bubble, it is now the object of variant 3 of the invention that a deformation generated by a macrobubble will not affect the quality of the cut. If a further optical breakthrough were placed at a defined position in deformed material or tissue, the position of the center of interaction within the material or tissue would be shifted as soon as said deformation is reduced by relaxation. Therefore, it is envisaged according to the third variant to keep the time between the application of laser energy in two areas of the material or of the tissue, respectively, influencing each other so small that it is smaller than a characteristic time for forming of macrobubbles. Said time is approximately 5 s. Of course, this approach is required only if two portions of the cut surface located adjacent to each other along the optical axis are present, because only then can a deformation caused by producing a cut surface portion have an effect on the formation of the other cut surface portion which is located adjacent thereto along the optical axis.

This approach is particularly important in generating a partial volume during the fs-LASIK method. This partial volume, also referred to as a lenticule, is generated by a posterior portion and an anterior portion of the cut surface, so that the cut surface as a whole circumscribes the lenticule. However, generating the posterior and anterior portions together within the characteristic time for forming the macrobubbles may result in relatively high demands on the scanning unit's speed of deflection or inevitably leads to special scanning paths. Preferably, this can be avoided by dividing the posterior and anterior portions into partial surfaces and skillfully selecting the processing sequence of these partial surfaces.

In one embodiment, the two areas are subdivided into annular partial surfaces. Since in the case of a lenticule the central partial surface has a much stronger influence on optical quality than the peripheral regions, first the cut corresponding to the central partial surface of the posterior portion and then that of the anterior portion is produced, so that the partial surfaces are formed immediately after each other. Then, the annular partial surface of the posterior portion, and that of the anterior portion is cut next. This principle can also be carried out with as many partial surfaces as desired. Practical limits are given by the fact that switching between the anterior and posterior portions always requires shifting of the laser focus along the optical axis, which for technical reasons takes up most of the time during scanning With this approach, it is important to note that the diameter of each annular or circular posterior partial surface should be somewhat larger than the diameter of the respective anterior partial surface generated next. This ensures that the posterior partial cut to be produced next makes not only anteriorly located disruption bubbles acting as centers of scattering impossible. The minimum amount by which the posterior partial cut has to be larger than its associated anterior partial cut is given by the numerical aperture of the focusing optics.

A further way of pushing the time interval below the characteristic time consists in generating the posterior portion with a spiral of the centers of interaction, said spiral extending from the outside to the inside, and in generating the anterior portion with a spiral extending from the inside to the outside. This ensures that portions located adjacent to each other along the optical axis are formed at least in the central region within the 5 s time interval. Of course, this method can be applied to the already mentioned divisions of partial surfaces.

It is therefore preferred that the control unit control the source of laser radiation as well as the scanning unit such that at least some of the portions adjacent to the optical axis are illuminated immediately subsequent to each other in time by sequential arrangement of the centers of interaction.

Analogous considerations also apply to the embodiment of the method according to the invention.

BRIEF DESCRIPTION OF THE DRAWINGS

The invention will be explained in more detail below, by way of example and with reference to the Figures, wherein.

DETAILED DESCRIPTION

Figure 1:
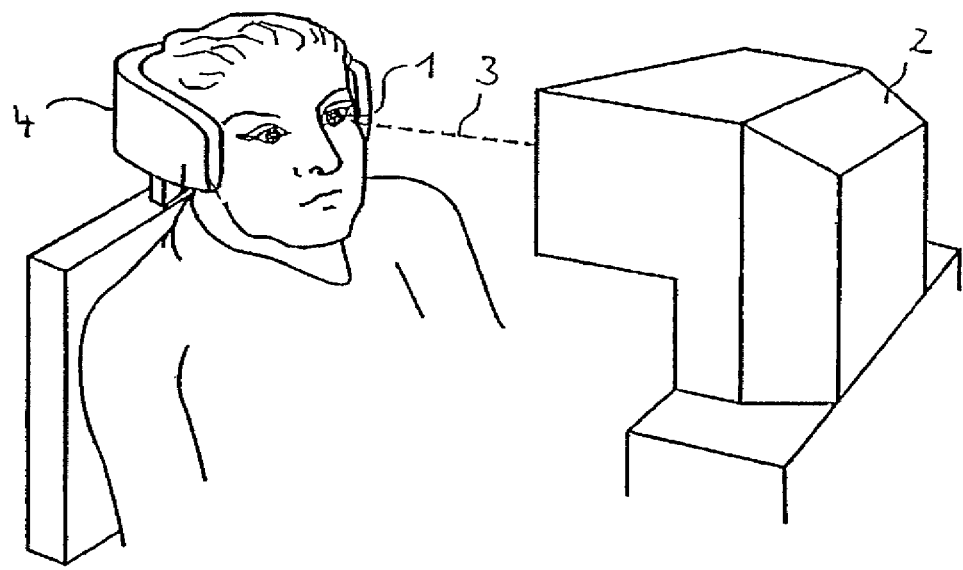
FIG. 1 shows a laser surgical instrument for eye treatment.

FIG. 1 shows a laser surgical instrument for treatment of a patient's eye 1, said laser surgical instrument 2 serving to effect a refractive correction. For this purpose, the instrument 2 emits a treatment laser beam 3 onto the eye of the patient 1 whose head is fixed in a head holder 4. The laser surgical instrument 2 is capable of generating a pulsed laser beam 3 such that the method described in U.S. Pat. No. 5,984,916 can be carried out. For example, the treatment laser beam 3 consists of fs-laser pulses having a pulse repetition rate of between 10 and 500 kHz. In the exemplary embodiment, the structural components of the instrument 2 are controlled by an integrated control unit.

Figure 2:
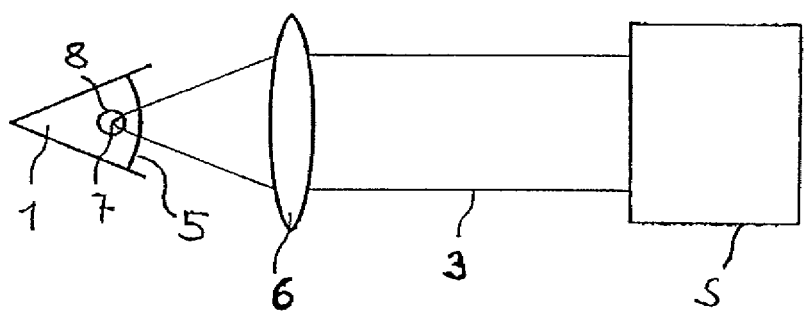
FIG. 2 shows a diagram of the effect of laser radiation on the cornea of the eye for the instrument of FIG. 1.

As schematically shown in FIG. 2, the laser surgical instrument 2 comprises a source of radiation S whose radiation is focused into the cornea 5 of the eye 1. Using the laser surgical instrument 2 a visual deficiency of the patient's eye 1 is corrected by removing material from the cornea 5 such that the refractive properties of the cornea change to a desired extent. In doing so, said material is removed from the corneal stroma which is located below the epithelium and the Bowman membrane as well as above the Decemet membrane and the endothelium.

Figure 3:
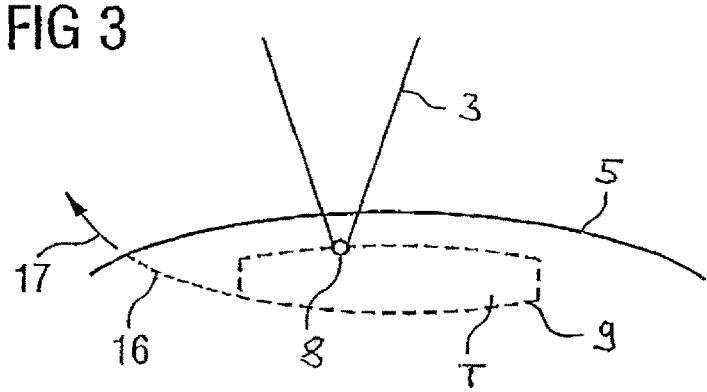
FIG. 3 shows a schematic view illustrating how a partial volume is generated and isolated by the instrument of FIG. 1.

Material removal is effected by separating material layers in the cornea using an adjustable telescope 6 to focus the high-enery pulsed laser beam 3 to a focus 7 located in the cornea 5. Each pulse of the pulsed laser radiation 3 generates an optical breakthrough in the tissue, such optical breakthrough in turn initiating a plasma bubble 8. Thus, the tissue layer separation covers a larger area than the focus 7 of the laser radiation 3, although the conditions for achieving the breakthrough are achieved only in the focus 7. Then, many plasma bubbles 8 are generated by suitable deflection of the laser beam 3 during treatment. This is shown schematically in FIG. 3. The plasma bubbles then form a cut surface 9 which circumscribes a partial volume T of the stroma, namely the material to be removed from the cornea 5. The cut surface 9 is formed by sequential arrangement of the plasma bubbles 8 as a result of a continuous shift in the focus 7 of the pulsed laser beam 3.

Due to the laser radiation 3 the laser surgical instrument 2 acts like a surgical knife directly separating material layers within the cornea 5 without damaging the surface of the cornea 5. If a cut 16 is guided up to the surface of the cornea by further generation of plasma bubbles 8, material of the cornea 5 isolated by the cut surface 9 can be pulled out laterally in the direction of the arrow 17 and can thus be removed.

Figure 4:
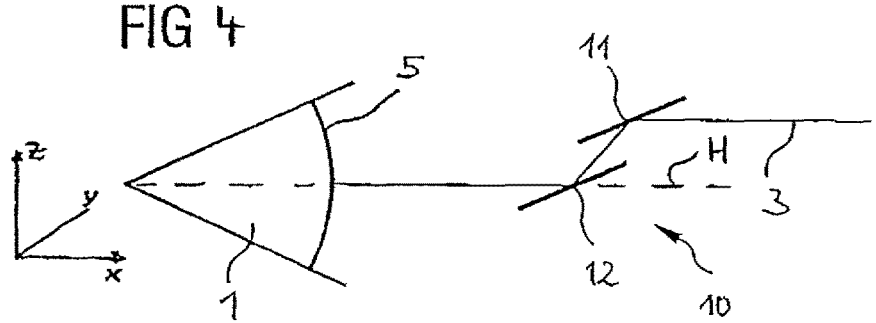
FIG. 4 shows a deflecting device of the instrument of FIG. 1.

On the one hand, displacement of the focus is then effected in the embodiment by means of the deflecting unit 10 shown schematically in FIG. 4, said deflecting unit 10 deflecting the laser beam 3, incident on an optical axis H of the eye 1, about two mutually orthogonal axes. For this purpose, the deflecting unit 10 uses a line mirror 11 as well as a frame mirror 12, which leads to two spatial axes of deflection located behind each other. The point of intersection of the optical axis H and the deflecting axis is then the respective point of deflection. On the other hand, the telesecope 6 is suitably adjusted for focus displacement. This allows the focus 7 to be shifted along three orthogonal axes in the x/y/z coordinate system shown schematically in FIG. 4. The deflecting unit 10 shifts the focus in the x/y plane, with the line mirror allowing to shift the focus in the x direction and the frame mirror allowing a shift in the y direction. In contrast thereto, the telescope 6 acts on the z coordinate of the focus 7. Thus, three-dimensional displacement of the focus 7 is achieved as a whole.

Due to the corneal curvature which is between 7 and 10 mm the partial volume T also has to be curved accordingly. Thus, the corneal curvature requires a curved cutting plane. This is effected by suitable control of the deflecting unit 10 and of the telescope 6.

Figure 5:
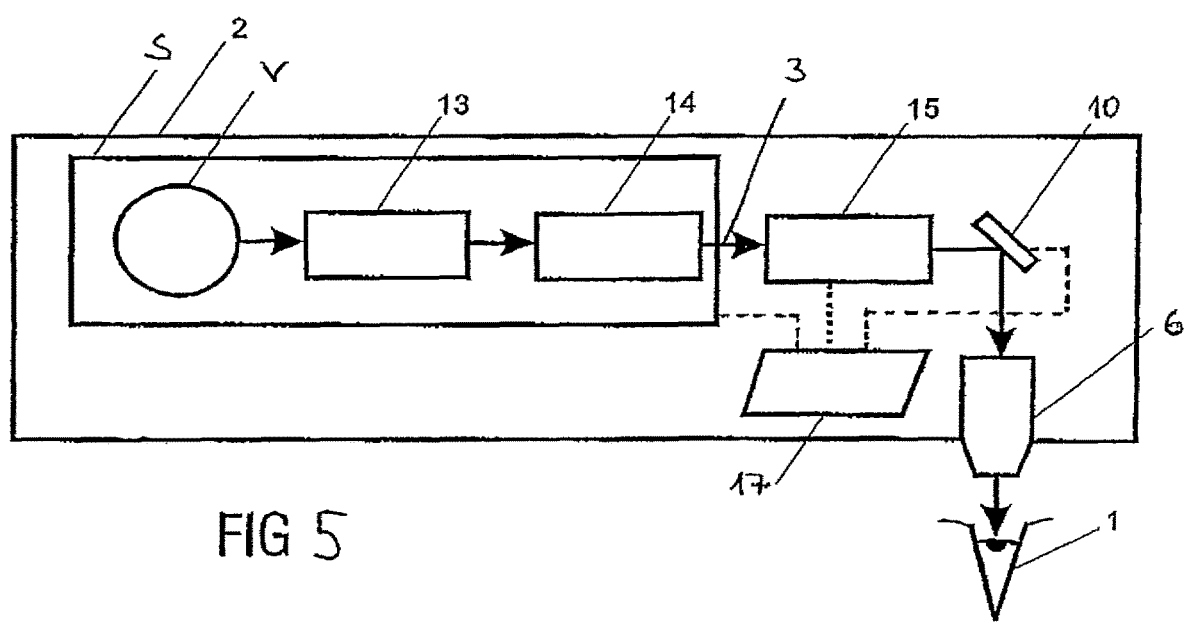
FIG. 5 shows a block diagram illustrating the structure of the instrument of FIG. 1.

FIG. 5 shows a simplified block diagram of the laser surgical instrument 2 for refractive surgery on the human eye 1. Only the most important structural components are shown: an fs laser serving as source of radiation S, which laser consists of an fs oscillator V as well as of one or more amplifying stages 13 and following which a compressor or pre-compressor 14 is arranged here as well; a laser pulse modulator 15 on which laser radiation from the laser S is incident; the deflecting unit 10, realized as a scanner here; an objective for focusing into the tissue to be treated, said objective realizing the telescope 6, and the control unit 17.

The laser S generates laser pulses having a duration in the fs range. First, the laser pulses reach the laser pulse modulator 15 which influences the laser pulses (in a manner yet to be described) according to a control signal from the control unit 17. Next, at least the treatment laser pulses reach the scanner 10 and pass through the objective 6 into the patient's eye 1. There, they are focused and generate optical breakthroughs in the focus 7. The modulator sets the energy of the laser pulses, i.e. the fluence of the individual laser pulses. As the modulator an AOM or an electro-optical modulator (EOM), a Pockels cell, a liquid crystal element (LC element), a fiber-optical switching element or a variable attenuator, e.g. a neutral density filter, may be used.

The laser surgical instrument 1 can then work in different modes of operation which may each be realized separately or in combination and which relate to the energy or the fluence F of each laser pulse or to the local distance at which the laser pulses are sequentially arranged so as to generate the cut surface 9.

Figure 6:
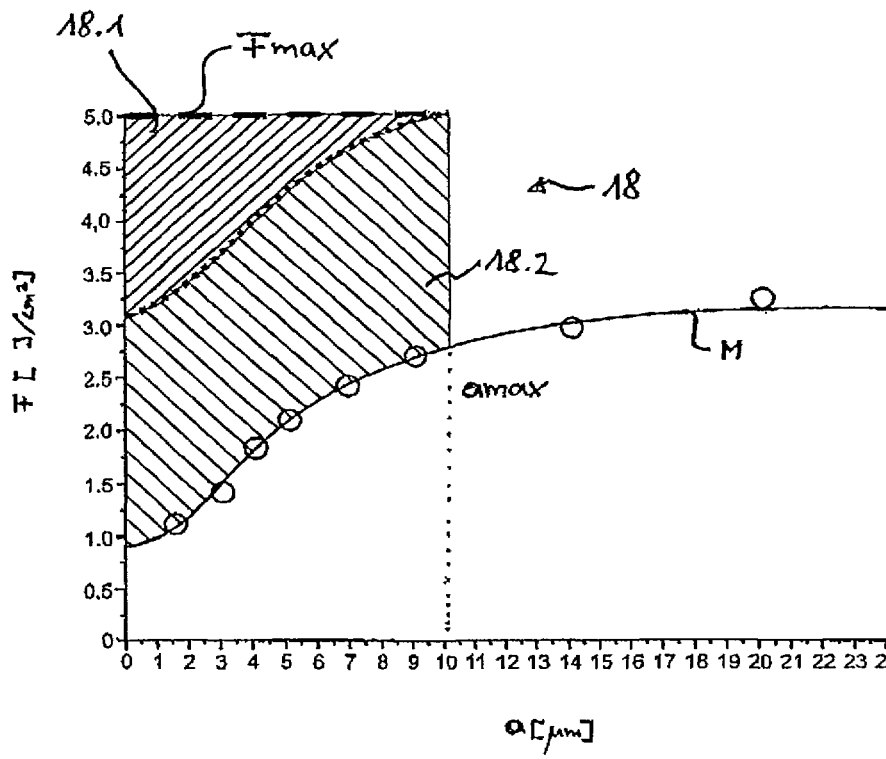
FIG. 6 shows a relationship between the distance of the centers of the optical breakthroughs generated by the instrument of FIG. 1 and the pulse energy, wherein possible operating ranges for the instruments of FIG. 1 are illustrated.

FIG. 6 shows a threshold value M as a graph illustrating the relationship between a spacing a at which the centers of interaction of the individual laser pulses are sequentially arranged within the eye's cornea 5 and the fluence F of each laser pulse. An optical breakthrough with an ensuing plasma bubble is generated only at a fluence above the threshold value.

The circles entered into the graph result from experimental measurements and represent points of measurement. Measurement was effected at a pulse duration of 300 fs and a 3 µm spot diameter of the focus 7.

The instrument 1 may be operated in an operational range 18 according to FIG. 6 which may be defined by various boundary conditions. The different definitions correspond to different variants of the invention. All variants are based on the course of the threshold value M for the fluence F as a function of the distance a. This dependence is approximated by the following formula:

$$M = 3.3 \; J/cm^2 - (2.4 \; J/cm^2)/(1+(a/r)^2),$$

wherein r is a parameter representing the average range of influence and is located between 3 and 10 µm, preferably 5 µm.

In a first variant, the instrument 1 works with a spacing a of the laser focuses 7, i. e. of the centers of interaction, which is below a maximum value $a_{max} = 10$ µm. From this value, the graph for the threshold value M drops considerably towards smaller spacings a, making it possible to work with a clearly reduced fluence F.

In a second variant, an upper limit $F_{max}$ is employed for the fluence F. The value for this is 5 $J/cm^2$.

In a combination of the first and second variants, both $a \leq a_{max}$ and $F \leq F_{max}$ apply. The spacings of the centers of interaction as well as the fluence of the laser pulses are located within the region composed of partial areas 18.1 and 18.2 which are yet to be explained. Since the laser surgical instrument 1, in both variants per se as well as in the combination of these two variants, respectively generates optical breakthroughs in the material, e.g. the cornea 5, the fluence F is, of course, always above the threshold value M, because each laser pulse securely generates an optical breakthrough 8 only above said threshold value.

A third variant modifies the second variant such that the fluence F of each laser pulse only exceeds the threshold value M at the most by an excessive energy of between 3 and 3.5 J/cm². The fluence F is then kept below the dotted line of FIG. 6 which separates the areas 18.1 and 18.2 from each other. Of course, the third variant can also be combined with the first variant, so that the fluence F and the spacing a are located in the hatched area 18.2.

In a different embodiment, the laser surgical instrument 1 works with laser pulses of which not every single one securely generates an optical breakthrough 8. However, in order to achieve material separation in spite of this, the centers of interaction are sequentially arranged at a spacing a which is smaller than the diameter d of the laser focus, i.e. smaller than the size of the zones of interaction. This mode of operation is shown in more detail in FIGS. 10-12.

Figure 7:
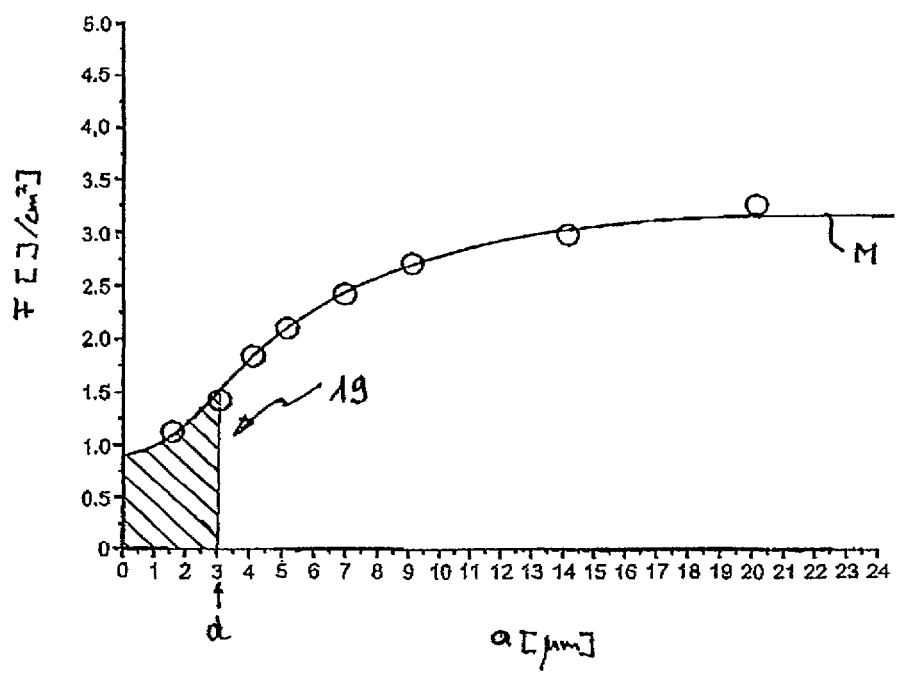
FIG. 7 shows a representation similar to that of FIG. 6.
Figure 10:
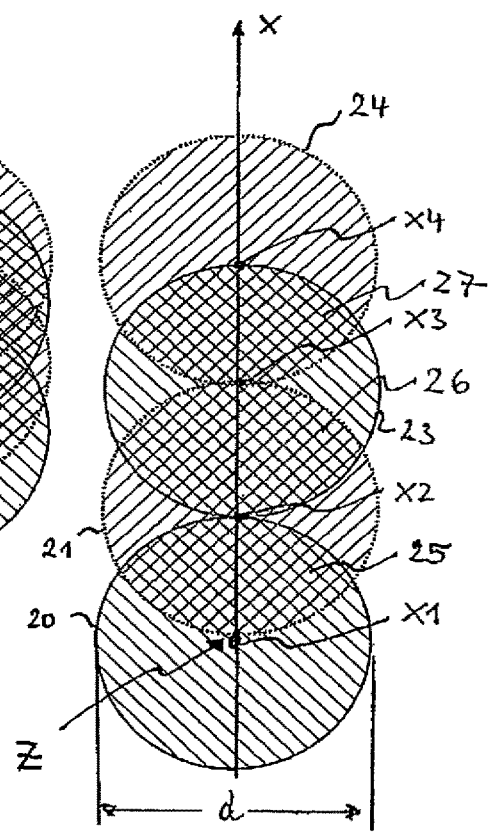
FIG. 10 shows a schematic view illustrating the arrangement of a plurality of zones of interaction when producing the cut surface with an instrument according to FIG. 1, and FIGS. 11 and 12 show views similar to that of FIG. 10 for modified modes of operation.

FIG. 10 shows a one-dimensional example of the arrangement of the centers of interaction Z corresponding to the position of the (theoretical) focal point. Each interaction is generated by a laser pulse, with the focus 7 being diffraction-limited, for example, and having the diameter d of 3 µm, for example, as assumed in FIG. 7. The centers of interaction, i.e. the center of the focused laser radiation, are then displaced such that adjacently covered zones of interaction 20, 21, 23 and 24 respectively overlap with their immediate neighbors. Thus, there are overlapping regions 25, 26, 27, which are each covered by two zones of interaction. The energy introduced into a zone of interaction is below the threshold value M, so that each of the zones of interaction 20-24 per se does not securely cause an optical breakthrough. However, due to said overlapping a material-separating effect is still achieved. Thus, it is essential for this mode of operation that the distance between the coordinates of the centers of interaction is smaller than the extent d of the zones of interaction. FIG. 10 clearly shows that the distance between the individual coordinates X1, X2, X3 and X4 corresponds to approximately half the diameter d of the zones of interaction 20-24, which results in a simple overlap.

Figure 11:
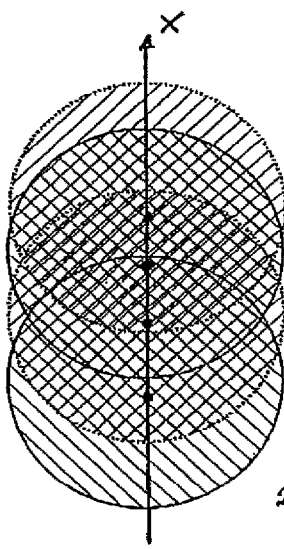

FIG. 11 shows a narrower graduation of the zones of interaction, ultimately resulting in a four-fold overlap of the zones of interaction. This allows a further reduction of the fluence F.

Figure 12:
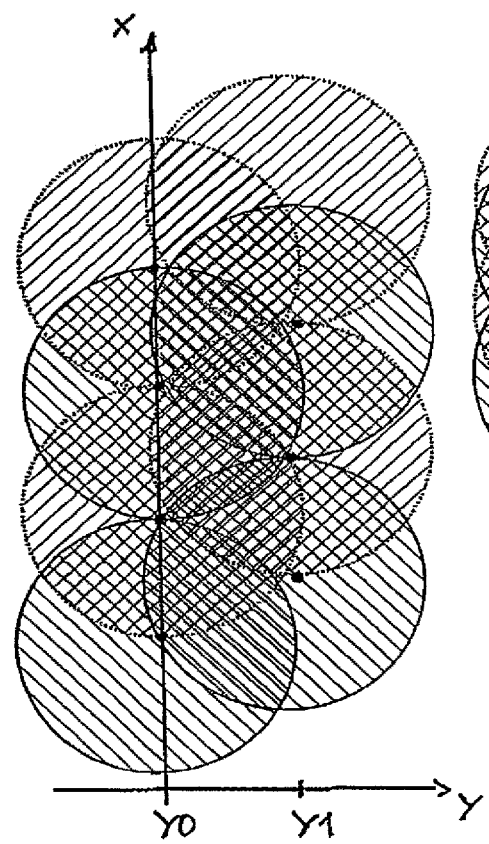

FIG. 12 illustrates that the representations of FIGS. 10 and 11 are only one-dimensional, i.e. considering only the x coordinate, for the sake of simplicity. If the zones of interaction overlapping each other in the x direction are displaced in the y direction, further overlaps will be achieved, so that in spite of the actually just one overlap in the x direction a three- or five-fold overlap of zones of interaction is achieved in the y direction, depending on the intervals. In this case, the selection of the intervals in the x direction or in the y direction, respectively, allows any desired factors of overlap (2, 3, 4, 5, 6, 7, . . . ).

As a result, the instrument 1 works in the operating range 19, which is characterized in that the distance between two subsequent centers of interaction is smaller than the extent of the zones of interaction or than the size of the focus spot and in that the fluence F is below the threshold value M required to generate optical breakthroughs.

In practice, a spacing of the laser focuses or of the centers of interaction, respectively, of approximately 3-5 µm has turned out to be well-suited for generating high-quality cuts with as little pulse energy as possible and requiring a limited amount of time.

In a laser surgical instrument 1 which produces very fine cuts, e.g. if the above-described fluence values are used for the laser pulses, the cut is not visible even immediately upon being produced, either because plasma bubbles or gas bubbles appear, having a smaller size and a shorter life than during operation outside the region 18, or because no bubbles form at all (during operation in the region 19). This may make it more difficult to prepare the isolated cut, e.g. by means of a spatula. A manual procedure used in many applications and wherein residual bridges which have not yet been fully separated are pierced by a spatula or other tools can become very difficult in case of such smooth cut.

Figure 8:
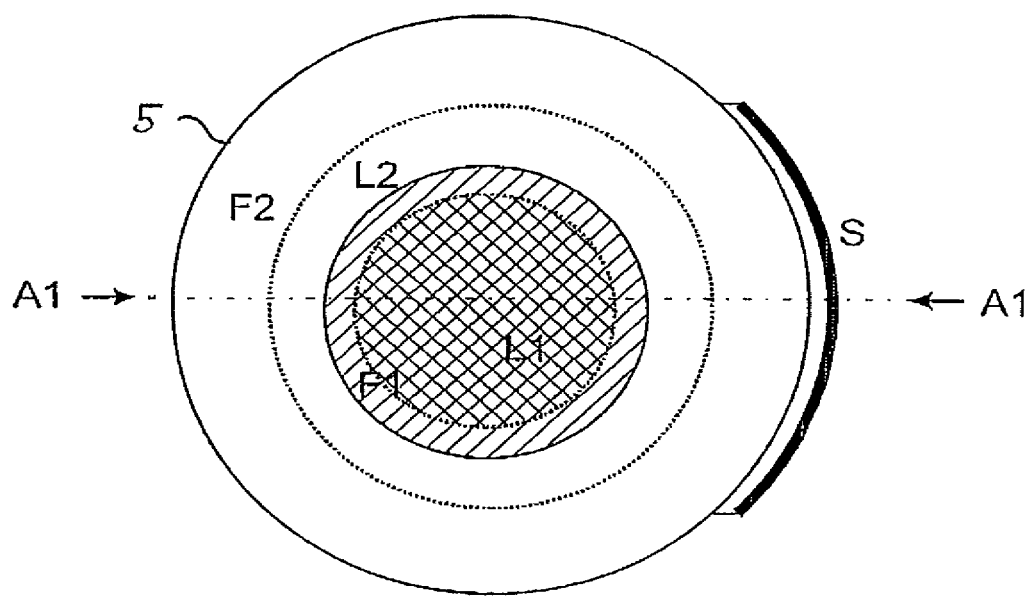
FIG. 8 shows a schematic top view of the eye's cornea for clearer illustration of the generated plasma bubbles' position or the cut surface caused thereby, respectively.
Figure 9:
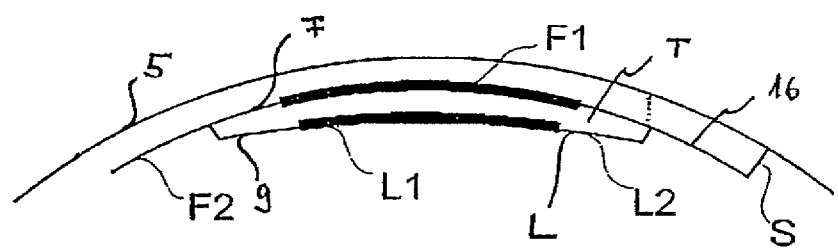
FIG. 9 shows a sectional view of the representation of FIG. 8 along the line A1-A1.

In order to avoid this, the control device 17 of the laser surgical instrument 1 carries out the division of the cut shown in FIGS. 8 and 9, for example. The cut surface is divided into partial cut surfaces having different degrees of fineness. These partial cut surfaces are cut with different smoothness so that regions form in which the cut surface has better optical visibility than in other regions.

FIG. 8 shows a top view of the cornea 5 of the patient's eye 1, and FIG. 9 shows a sectional view along line A1-A1 of FIG. 8. As can be seen, the cut surface 9 is adapted to isolate the partial volume T, as already schematically indicated in FIG. 3. The cut surface 9 then consists of an anterior portion F and a posterior portion L. The anterior portion F is guided up to a peripheral opening S via a laterally opening cut 16 leading up to the corneal surface. Thus, after forming the cut surface 9 the portions F, L, 16 and S of the lens-shaped partial volume T are located in a pocket formed by the peripheral opening S.

In order that a surgeon may feel this pocket with a spatula or other surgical instrument so as to sever possible bridges of tissue between the lens-shaped partial volume T and the rest of the cornea 5, the anterior portion F as well as the posterior portion L are respectively divided into two partial regions. A core region F1 or L1, which is substantially circular, is respectively surrounded by an annular peripheral region F2 or L2. In the core region located near the optical axis of vision, a small size of plasma bubble, i.e. a fine line of cutting, is worked with. This may be effected, for example, by operation in the regions 18 or 19 of FIGS. 6 and 7, respectively. In contrast thereto, a comparatively coarser cut is produced in the (annular) peripheral regions L2 and F2, for example by deliberately working outside the regions 18 or 19, so that relatively large plasma bubbles form. Thus, in these peripheral regions, the cut surface is a lot rougher and easier to recognize by the surgeon.

The diameters of the central regions F1 and L1 are preferably greater than the pupil diameter P of the treated eye. Thus, the peripheral regions F2 and L1, where a rougher cut was employed, are located outside the region of the cornea 5 used for optical perception and accordingly do not have a disturbing effect. The purpose of dividing the portions L and F is to simultaneously achieve the aspect of maximum precision of cutting as well as of good handling due to the visibility of the cut in the peripheral region as a result of differences in processing.

If plasma bubbles are employed for material separation, the energy of the laser pulses is above the threshold value M. As already mentioned, the shape of the bubbles resulting from the absorption of the laser energy in the tissue is subject to change over time. A first phase in which individual bubbles form is followed by a phase of agglomeration in which several individual bubbles join to form larger macrobubbles. Finally, dissipation is noted as the last phase in which the gas content of the macrobubbles is absorbed by the surrounding tissue until the bubbles have finally vanished again completely. Now, macrobubbles have the adverse property of deforming the surrounding tissue. If a further center of interaction is placed at a certain position in the deformed tissue to form the beginning of a plasma bubble, the position of the center of interaction will change and so will the position of the tissue separation effected thereby as soon as the phase of dissipation begins, in which the bubbles disappear and the deformed tissue relaxes (at least partially). Since the macrobubbles form only after a characteristic time and are not present already upon introducing laser pulse energy, it is envisaged for one variant of the laser surgical instrument 1 that the time between application of the laser energy in two regions of the tissue potentially influencing each other be kept sufficiently short so as to be shorter than a characteristic time which is required to form macrobubbles.

During isolation of the lens-shaped partial volume T, regions of the posterior and anterior portions of the cut surface 9 having an adverse effect on each other are located in the region of the optical axis of vision. If the cut is produced in the anterior portion F of the cut surface 9 only at a time when the previously processed posterior portion L already comprises macrobubbles, the cut surface of the anterior portion F is located within deformed tissue. The result after relaxation would be an undesired undulation of the cut surface 9 in the anterior portion F. Therefore, the laser surgical instrument 1 produces the cut surface in the anterior portion F and in the posterior portion L within a time interval which is smaller than the characteristic time it takes for macrobubbles to form. Typically, such time is approximately 5 s.

One way of achieving this consists in dividing the anterior and posterior portions into corresponding partial surfaces and alternating between the partial surfaces of the posterior and anterior portions during production of the cut surface so that at least in the central region the characteristic time for producing partial surfaces, posteriorly and anteriorly, is not exceeded. A further possibility consists in a suitable sequential arrangement of the centers of interaction. Thus, for example, first the posterior portion L can be cut in a spiral leading towards the optical axis of vision from the outside to the inside and directly afterwards the anterior portion F can be cut in a spiral extending outwards from the axis of vision. The generated interactions, at least in a core region around the axis of vision, are then within the time frame given by the characteristic period of time so that there is no influence on the macrobubbles during processing of the anterior portion.

During division into the partial surfaces which the laser surgical instrument 1 effects under the control of the control device 17 it is ensured that a posterior region to be worked on is not disturbed by an already processed anterior surface or zone of interaction acting as a scattering center.

The described cut shapes, surface divisions, etc. are effected by the laser surgical instrument under the control of the control device 17. The control device 17 causes operation of the laser surgical instrument 1 by the process features described herein.

As far as embodiments of the laser surgical instruments have been described above, they can be realized alone as well as in combination, depending on the specific realization of the laser surgical instrument 1. Instead of being employed in laser surgery, the instrument 1 can also be used for non-surgical material processing, for example in the production of wave guides or the processing of flexible materials.

The invention claimed is:

1. A device for material processing by laser radiation, said device comprising:
    a source of laser radiation emitting pulsed laser radiation for interaction with the material;
    optics focusing the pulsed laser radiation to a center of interaction in the material;
    a scanning unit shifting positions of the center of interaction within the material, wherein each laser pulse interacts with the material in a zone surrounding the center of interaction assigned to said laser pulse so that material is separated in the zones of interaction; and
    a control unit which controls the scanning unit and the source of laser radiation such that a cut surface is produced in the material by sequential arrangement of zones of interaction, wherein the spatial distance a of the centers of interaction of two subsequent laser pulses is smaller than a size d of the focus so that sequentially produced zones of interaction overlap in the material and the fluence F of each laser pulse is below a threshold value M, above which an optical breakthrough forms in the material.

2. The device as claimed in claim 1, wherein adjacent centers of interaction are located at a spatial distance of less than or equal to 10 µm from each other.

3. The device as claimed in claim 1, wherein for each center of interaction the laser pulse fluence F is below 5 J/cm$^2$.

4. The device as claimed in claim 1, wherein the control unit controls the source of laser radiation and the scanning unit such that the cut surface is complemented by an additional cut surface, which is formed by control of the source of laser radiation so as to cause a laser pulse fluence F greater than 3 J/cm$^2$.

5. The device as claimed in claim 1, wherein the control unit controls the source of laser radiation and the scanning unit such that the cut surface is complemented by an additional cut surface, which is formed by control of the source of laser radiation so as to cause a laser pulse fluence F greater than 5 J/cm$^2$.

6. The device as claimed in claim 5, wherein the control unit controls the source of laser radiation and the scanning unit such that the additional cut surface surrounds the cut surface.

7. The device as claimed in claim 1, wherein the fluence of each laser pulse is below a threshold value M, which is given as $$M = 3.3\ J/cm^2 - (2.4\ J/cm^2)/(1+(a/r)^2)$$

where a is the the spacing between two adjacent centers of interaction and r is a parameter, with 3 µm≤r≤10 µm.

8. A method of material processing by laser radiation, comprising generating and focusing pulsed laser radiation focused at centers of interaction in the material; and shifting positions of the centers of interaction in the material, each laser pulse interacting with the material in a zone surrounding the center of interaction assigned to said laser pulse, so that material is separated in the zones of interaction, and a cut surface is produced in the material by sequential arrangement of zones of interaction, wherein the spatial distance a of the centers of interaction of two subsequent laser pulses is smaller than a size d of the focus so that sequentially produced zones of interaction overlap in the material and the fluence F of each laser pulse is below a threshold value M, above which an optical breakthrough forms in the material.

9. The method as claimed in claim 8, wherein adjacent centers of interaction are located at a spatial distance of less than or equal to 10 μm from each other.

10. The method as claimed in claim 8, wherein the zones of interaction are illuminated with pulses each having a fluence F of less than 5 J/cm².

11. The method as claimed in claim 8, wherein the cut surface is complemented by an additional cut surface, which is produced at a laser pulse fluence F greater than 3 J/cm².

12. The method as claimed in claim 8, wherein the cut surface is complemented by an additional cut surface, which is produced at a laser pulse fluence F greater than 5 J/cm².

13. The method as claimed in claim 11, wherein the additional cut surface surrounds the cut surface.

14. The method as claimed in claim 8, wherein the fluence F is below a threshold value M given as $$M = 3.3 \ J/cm^2 - (2.4 \ J/cm^2)/(1+(a/r)^2)$$

wherein a is the spatial spacing of the centers of interaction and r is a parameter, with 3 μm ≤ r ≤ 10 μm.

15. The method as claimed in claim 8, wherein the material is tissue of an eye.

16. The device a claimed in claim 1, wherein the control unit controls the source of laser radiation and the scanning unit such that the cut surface comprises two portions located adjacent to each other along the optical axis and irradiates the two portions at least partially with laser radiation pulses applied within a time interval t less than or equal to five seconds.

17. The device as claimed in claim 16, wherein the control unit divides portions of the cut surface located adjacent to each other along the optical axis into respective partial cut surfaces and controls the source of laser radiation and the scanning unit such that partial cut surfaces located adjacent to each other along the optical axis are irradiated with laser radiation immediately following each other in time by sequential arrangement of the centers of interaction.

18. The method as claimed in claim 8, wherein the cut surface is provided with two portions located adjacent to each other along the optical axis, which portions are irradiated at least partially with laser pulses applied within a time interval t less than or equal to five seconds.

* * * * *

UNITED STATES PATENT AND TRADEMARK OFFICE
CERTIFICATE OF CORRECTION

PATENT NO. : 11,033,980 B2  
APPLICATION NO. : 13/715670  
DATED : June 15, 2021  
INVENTOR(S) : Mark Bischoff et al.

It is certified that error appears in the above-identified patent and that said Letters Patent is hereby corrected as shown below:

In the Claims

Column 14, Line 54, delete "the the" and insert --the--

Column 16, Line 3, delete "a" and insert --as--

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*